US008609436B2

(12) United States Patent
Barnardo et al.

(10) Patent No.: US 8,609,436 B2
(45) Date of Patent: Dec. 17, 2013

(54) METHOD

(75) Inventors: Martin C. N. M. Barnardo, Oxford (GB); Andrea W. Harmer, Sheffield (GB); Michael Bunce, Bromborough (GB); Robert W. Vaughn, London (GB); Kenneth I. Welsh, London (GB)

(73) Assignees: Guy's & St Thomas' Hospital NHS Trust ("GST"), London (GB); King's College London, London (GB); Oxford Radcliffe Hospital NHS ("ORH") Trust of the John Radcliffe Hospital, Oxford (GB)

( * ) Notice: Subject to any disclaimer, the term of this patent is extended or adjusted under 35 U.S.C. 154(b) by 0 days.

(21) Appl. No.: 09/809,029

(22) Filed: Mar. 16, 2001

(65) Prior Publication Data

US 2003/0017447 A1 Jan. 23, 2003

Related U.S. Application Data

(60) Provisional application No. 60/190,027, filed on Mar. 17, 2000.

(51) Int. Cl.
*G01N 33/543* (2006.01)
(52) U.S. Cl.
CPC ........... *G01N 33/543* (2013.01); *Y10S 435/975* (2013.01)
USPC ........... 436/518; 435/7.1; 435/7.92; 435/975; 436/501; 436/524
(58) Field of Classification Search
USPC ............... 435/5, 6, 7.1, 7.24, 7.92, 975, 69.3, 435/69.7; 436/518, 524, 506, 513, 528; 530/300, 333
See application file for complete search history.

(56) References Cited

U.S. PATENT DOCUMENTS

| | | | |
|---|---|---|---|
| 4,554,088 A | | 11/1985 | Whitehead et al. |
| 4,693,985 A | * | 9/1987 | Degen et al. ................... 436/531 |
| 4,810,632 A | | 3/1989 | McMillan |
| 5,110,726 A | | 5/1992 | Ogden |
| 5,180,661 A | | 1/1993 | Brubaker |
| 5,223,397 A | | 6/1993 | Pouletty et al. |
| 5,256,543 A | | 10/1993 | Pouletty et al. |
| 5,270,169 A | * | 12/1993 | Chang et al. .................. 435/7.24 |
| 5,292,641 A | * | 3/1994 | Pouletty ........................ 435/7.24 |
| 5,403,745 A | * | 4/1995 | Ollington et al. .............. 435/11 |
| 5,420,013 A | | 5/1995 | Pouletty et al. |
| 5,420,016 A | * | 5/1995 | Boguslaski et al. ............ 435/12 |
| 5,514,557 A | | 5/1996 | Moghaddam |
| 5,948,627 A | | 9/1999 | Lee et al. |
| 6,046,013 A | * | 4/2000 | Tidey et al. ................... 435/7.21 |
| 6,060,309 A | * | 5/2000 | Kindsvogel et al. ........... 435/325 |
| 6,150,122 A | | 11/2000 | Lee et al. |
| 6,171,585 B1 | | 1/2001 | Jordan et al. |
| 6,218,363 B1 | * | 4/2001 | Baserga et al. ................ 514/15 |
| 6,232,445 B1 | | 5/2001 | Rhode et al. |
| 6,297,062 B1 | | 10/2001 | Gombinski |
| 6,528,304 B1 | * | 3/2003 | Carosella et al. .............. 435/325 |
| 6,727,070 B2 | * | 4/2004 | Thomas et al. ................. 435/7.1 |
| 7,125,964 B2 | | 10/2006 | Luxembourg et al. |
| 7,265,218 B2 | | 9/2007 | Burrows et al. |
| 2003/0125657 A1 | | 7/2003 | Koll et al. |
| 2003/0166057 A1 | | 9/2003 | Hildebrand et al. |
| 2004/0137617 A1 | * | 7/2004 | Luxembourg et al. ......... 435/372 |
| 2004/0191245 A1 | | 9/2004 | Barnardo et al. |
| 2005/0074853 A1 | | 4/2005 | Burrows et al. |
| 2007/0141050 A1 | | 6/2007 | Barnardo et al. |
| 2008/0057521 A1 | | 3/2008 | Barnardo et al. |

FOREIGN PATENT DOCUMENTS

WO    WO 95/33995    12/1995
WO    WO 98/10284 A1    3/1998

OTHER PUBLICATIONS

Tan et al. (A novel, highly efficient peptide-HLA clas I binding assay using unfolded heavy chain molecules: identification of HIV-1 derived peptides that bind to HLA-A 0201 and HLA-A 0301), Journal of Immunological Methods 205 (2) (1997) 201-209.*
Walter et al, Stimulation of human cytotoxic T cells with HIV-1 derived peptides presented by recombinant HLA-A2 peptide complexes, International Immunology, vol. 9, No. 3, pp. 451-459, 1997.*
Barnardo et al., Detection of HLA antibodies using single recombinant HLA alleles, Human Immunology, Abstracts, 1999, vol. 60, Supplement 2, 7.4, p. S9.*
Barnardo et al., Detection of HLA-Specific IgG using single, recombinant HLA alleles, Human Immunology,(1999) vol. 60, No. Suppl. 1, p. S1.*
Arimilli et al., Refolding and Reconsititution of Functionally Active Complexes of Human Leukocyte Antigen DR2 and Myeline Basic protein Peptide from Recombinant a and b Polypeptide chains, The Journal of Biol. Chem. vol. 270, pp. 971-977, 1995.*
Frayser et al., Empty and Peptide-Loaded Class II Major Histocompatibility Complex Proteins Produced by Expression in *Escherichia coli* and Folding in Vitro, Protein Expression and Purification 15, 105-114, 1999.*
Arguello et al., A novel method for simultaneous high resolution identificatin of HLA-A, HLA-B, and HLA-Cw alleles, Proc. Natl. Acad. Sci. USA, vol. 93, pp. 10961-10965, Oct. 1996.*
Barnardo, et al., Detection of HLA-specific IgG antibodies using single recombinant HLA alleles: the MonoLisa assay, *Transplantation*, 2000, pp. 531-6, vol. 70(3), Lippincott Williams & Wilkins, Inc., USA.
Kao et I., Enzyme-linked Immunoassay for anti-HLA antibodies— an alternative to panel studies by lumphocytoxicity, *Transplantation*, 1993, pp. 192-196, vol. 55(1), Williams & Wilkins, USA.
Terasaki et al., Microdroplet Assay of Human Serum Cytotoxins, *Nature*, 1964, pp. 998-1000, vol. 204.
Carroll et al., "Optimal fixation of cells for use in solid-phase ELISA", *Journal of Immunological Methods*, 1990, pp. 71-76, vol. 129, Elsevier Science Publishers B.V.

(Continued)

*Primary Examiner* — Gary W Counts (57) ABSTRACT

The invention provides a method of detecting the presence of anti-MHC antibodies in a sample comprising contacting said sample with one or more recombinant MHC molecules or functionally equivalent variants, derivatives or fragments thereof and detecting the binding or absence of binding of antibodies to said recombinant MHC molecules. This method allows the detection and/or identification of one or more specific MHC particularly HLA allele antibodies.

24 Claims, 3 Drawing Sheets

(56) References Cited

OTHER PUBLICATIONS

Beulow et al., "Soluble HLA antigens and ELISA—a new technology for crossmatch testing," *Transplantation*, 1995, pp. 1594-1599, vol. 60(12), Williams & Wilkins, USA.

Ogg et al., "High frequency of skin-homing melanocyte-specific cytotoxic T lymphocytes in Autoimmune Vitiligo," *J. Exp. Med.*, 1998, pp. 1203-1208, vol. 188(6), The Rockefeller University Press, USA.

Harmer et al., "A highly sensitive, rapid screening method for the detection of antibodies directed against HLA class I and II antigens," *Transplant International*, 1993, pp. 277-280, vol. 6, Springer-Verlang.

McKenna et al., "Anti-HLA antibodies after solid organ transplantation," *Transplantation*, 2000, pp. 319-326, vol. 69(3), Lippincott Williams & Wilkins, Inc., USA.

O'Rourke et al., "Flowcytometry cross-matching as a predictor of acute rejection in sensitized recipients of Cadaveric renal transplants," *Clinical Transplantation*, 2000, pp. 167-173, vol. 14(2), Munksgaard.

Parham, "Typing for Class I HLA polymorphism: past, present, and future," *European Journal of Immunogenetics*, 1992, pp. 347-359, vol. 19.

Bodmer et al., "Nomenclature for factors of the HLA system," Tissue Antigens, 1999, pp. 407-446, vol. 53, Munksgaard International Publishers, Ltd.

Altman et al., "Phenotypic Analysis of antigen-specific T-lympocytes," *Science*, 1996, pp. 94-96, vol. 274.

Harmer et al., "Detection of HLA-Specific IgG using single recombinant HLA alleles," abstract participants of British Transplantation 2nd Annual Congress, Mar. 29-31, 1999.

Papassavas et al., "Is There MHC Class II Restriction of the Response to MHC Class I in Transplant Patients," *Transplanation*, Feb. 27, 2002, pp. 642-651, vol. 73, No. 4. Lippincott Williams & Wilkins, Inc., USA.

Sato, et al., "Determinants of the Peptide-induced Conformational Change in the Human Class II Major Histocompatibility Complex Protein HLA-DRI", The Journal of Biological Chemistry, vol. 275, No. 3, Jan. 21, 2000, pp. 2165-2173.

Viken, et al., "Influence on Antibody Recognition of Amino Acid Substitutions in the Cleft of HLA-DQ2 Molecules; Suggestive Evidence of Peptide-Dependent Epitopes," Human Immunology, vol. 44, 1995, pp. 63-69.

Zhang, et al., "Solvent exposed side chains of peptides bound to HLA A*1101 have similar effects on the reactivity of alloantibodies and specific TCR", International Immunology, vol. 8, No. 6, Mar. 7, 1996, pp. 927-938.

Altman, et al., "Formation of Functional Peptide Complexes of Class II Major Histocompatibility Complex Proteins From Subunits Produced in *Escherichia coli*", *PNAS USA* 90 Nov. 1, 1993, 10330-10334.

Austin, Penelope et al., "Functional expression of HLA-DP genes transfected into mouse fibroblasts", *Nature* vol. 313, No. 5997 1985, 61-64.

Claesson-Welsh, et al., "Implications of the Invariant-Gamma-Chain on the Intracellular Transport of Class II Histocompatibilitly Antigens", *J. Immunol.* 135 (5) 1985, 3551-3557.

Gauthier, et al., "Expression and Crystallization of the Complex of HLA-DR2 (DRA, DRB1*1501) and an Immunodominant Peptide of Human Hyelin Basic Protein", *PNAS* 95 (20) Sep. 29, 1998, 11828-11833.

Koppelman, et al., "Rapid Nonlysosomal Degradation of Assembled HLA Class II Glycoproteins Incorporating a Mutant DR Alpha-Chain", *J. Immunol.* 145 (8) 1990, 2730-2736.

Kvist, et al., "Membrane Insertion and Oligomeric Assembly of HLA-DR histocompatibility Antigens", *Cell* vol. 29 May 1982, 61-69.

Lawrance, et al., "The Genomic Organisation and Nucleotide Sequence of the HLA-SB(DP) Alpha Gene", *Nucleic Acids Res.* 13 (20) 1985, 7515-7528.

Long, et al., "Isolation of cDNA Clones for the P33 Invariant Chain Associated with HLA-DR Antigens", *Proc. Natl. Acad. Sci. USA* 80 (18) 1983, 5714-5718.

Marsh, Steven G. et al., "HLA class II nucleotide sequences", *Tissue Antigens* vol. 40, No. 5 Nov. 1992, 229-243.

Miller, et al., "Efficient Cell Surface Expression of Class II MHC Molecules in the Absence of Associated Invariant Chain", *J. Exp. Med.* 164 1986, 1478-1489.

Schaiff, et al., "HLA-DR Associates with Specific Stress Proteins and is Retained in the Endoplasmic Reticulum in Invariant Chain Negative Cells", *J. Exp. Med.* 176 (3) 1992, 657-666.

Stern, et al., "The Human Class II MHC Protein HLA-DR1 Assembles as Empty Alpha Beta Heterodimers in the Absence of Antigenic Peptide", *Cell* 68 1992, 465-477.

Tan, et al., "Novel, Highly Efficient Peptide-HLA Class I Binding Assay Using Unfolded heavy Chain Molecules: Identification of HIV-1 Derived Peptides that Bind to HLA-A* 0201 and HLA-A* 0301", *Journal of Immunological Methods* 205 (2) 1997, 201-209.

Wake, et al., "Isolation of cDNA Clones Encoding HLA-DR Alpha Chains", *Proc. Natl. Acad. Sci. USA* 79 (22) 1982, 6979-6983.

Wettstein, et al., "Expression of a Class II Major Histocompatibility Complex (MHC) Heterodimer in a Lipid-Linked Form with Enhanced Peptide/Soluble MHC Complex Formation at Low pH.", *J. Exp. Med.* 174 1991, 219-228.

Young, et al., "Epitope Recognition by a DP Alpha Chain-Specific Monoclonal Antibody (DP11.1) is Influenced by the Interaction Between the DP Alpha Chain and its Polymorphic DP Beta Chain Partner", *Hum. Immunol.* 23 (1) 1988, 37-44.

EP07015960.3 OAR-4MO, Aug. 12, 2008, 1 page.

Barnardo, Martin C. et al., "Detection of HLA-Specific IGG antibodies using single recombenant HLA alleles", *Transplantation*, vol. 70, Aug. 2000, pp. 531-536.

Devito, L. D. et al., "Adsorption of cytotoxic anti-hla antibodies ith HLA class i immunosorbant beads", *transplantation*, vol. 49(5), May 1990, pp. 925-931.

Kao, Kuo-Jang et al., "Enzyme-Linked Immunoassay for Anti-HLA Antibodies—an Alternative to panel Studies by Lymphocytotoxicity", *Transplantation*, vol. 55, No. 1, Williams & Wilkins, USA, Jan. 1993, pp. 192-196.

Kraiba, Radhia et al., "HLA-DR and DQ antigens in chronic lymphocytic leukemia: dissociation of expression revealed by cell surface, protein, and mRNA studies.", *Leukemia*, vol. 3, No. 5, May 1989, pp. 386-393.

Whitcombe, David et al., "Detection of PCR products using self-probing amplicons and fluorescence", *Nature Biotechnology* vol. 17 pp. 804-807, Aug. 1999, pp. 804-807.

Wolpl, A et al., "Human monoclonal antibody with T-cell-like specificity recognizes MHC class I self-peptide presented by HLA-DR1 on activated cells.", *Tissue Antigens*, vol. 51, No. 3, Mar. 1998, pp. 258-269.

Pei, R. et al., "Flow Cytometric Detection of HLA Antibodies Using a Spectrum of Microbeads", *Human Immunology*, vol. 60, Issue 12, American Society for Histocompatibility and Immunogenetics, Dec. 1999, 1293-1302.

* cited by examiner

METHOD

This application claims priority from U.S. Provisional Application No. 60/190,027, filed Mar. 17, 2000.

The present invention relates to a method for detecting anti Major Histo-Compatibility Complex (MHC) antigen, particularly anti-human leucocyte antigen (HLA) reactive antibodies.

BACKGROUND OF THE INVENTION

MHC antigens are glycoproteins expressed on the surface of cells, such as platelets, macrophages and lymphocytes. Functionally, these molecules play important roles in the presentation of foreign antigenic peptides to cytotoxic T cells. MHC molecules are divided into two types, Class I and Class II, based on their structure and function. MHC Class I genes encode glycoproteins which are expressed on the surface of almost all nucleated cells of the body. MHC Class I molecules are involved in activating cytotoxic T cells. MHC Class II genes encode glycoproteins expressed primarily on antigen presenting cells (macrophages, dendritic cells, B cells) where they present the processed antigen (e.g. viral or other foreign antigens) to the T helper cells. These antigens form one group of the so-called histocompatibility antigens.

MHC molecules in humans are referred to as Human leucocyte Antigen (HLA) molecules. Typing of the numerous HLA molecules present in humans has shown that individuals possess a particular 'signature' of HLA molecules present on their cells. HLA molecules are coded for in the human genome by a series of four gene loci. HLA Class I molecules are coded for by the A, B, C, E, F and G regions whereas the HLA Class II molecules are coded for by the DR, DQ, DP, DO and DM regions. The loci constituting the HLA molecules are highly polymorphic, and many alternate forms of the gene or alleles exist at each locus.

In normal immune responses self-MHC, e.g. HLA molecules are recognised by T cell receptors in vivo. The T cell receptors see the foreign antigen expressed as a small peptide in the context of a MHC Class I or class II molecule. This leads to production of appropriate antibody responses to the foreign antigen or destruction of the presenting cell depending on the presenting and T cells which are involved.

The immune System is however also able to identify and mount a challenge to non-self, i.e. foreign MHC molecules. Thus, when presented with a non-host MHC molecule, the immune system will react to destroy cells carrying the non-host MHC by normal immunological means, i.e. produce antibodies, activate the complement system etc. This is obviously undesirable when the cells carrying the non-host MHC, e.g. L are purposively introduced, for example, foreign cells or tissue, e.g. in a transplanted organ and presents a bar to the introduction of such cells.

Placing a 'foreign' (i.e. non-host) MHC molecule into an individual may result in the individual producing anti-MHC antibodies which will bind specifically to that MHC. Individuals may raise anti-MHC antibodies, and become "sensitized", if they are exposed to a foreign MHC, i.e. during pregnancy, by blood transfusion, or by receiving an organ donation.

Pre-sensitization to MHC via transfusion, transplantation, or pregnancy can cause rapid rejection of transplanted tissue or poor platelet survival after transfusion. Therefore, testing for anti-MHC antibodies prior to tissue or organ transplantation is of great importance, as the presence in the recipient of anti-MHC antibodies which bind to donor MHC molecules (donor specific crossmatch) is predictive of a high risk of rejection of the transplanted tissue or organ. Thus, prior to transplantation, the donor tissue is typed for MHC molecules, and the recipient is typed for anti-MHC antibodies. Screening of potential transplant recipients for anti-HLA antibodies is an essential part of the pre-transplant monitoring carried out by tissue-typing laboratories.

Ideally, organs would be transplanted that are an ideal HLA match to the recipient. However, in view of the high number of HLA genes involved, up to hundred or more alleles for each, a perfect match is very difficult to obtain.

Post-transplant monitoring is also valuable to assess the level of anti-MHC antibodies which are being generated and hence the continued success or likely rejection of a transplant.

Anti-HLA antibody testing methods are known in the art, and include the screening of the blood or serum from the potential recipient against a panel of cello which are considered to present a representative selection of HLA antigens. This procedure can take up to 6 weeks. Such screening determines the panel reactivity (PR) for each sample, and gives an estimate of the degree of sensitisation against the panel of cello used for testing and can be related to the chance of a donor being suitable. The panel size may range from 25 to 100 different cells, and the larger the panels (50 to 100 different cells), the more reliable the results.

A more specific method is complement-dependent-lymphocytotoxicity (CDC) testing. In this method, the serum or blood of the potential recipient is tested against a panel of lymphocytes (or more specifically, the donor's lymphocytes) and the mixture is further incubated with complement factors. In order to measure the level of cytotoxicity, the viable and non-viable cells are distinguished using a dye. Therefore, this method is not without drawbacks, as the discrimination between living and dead cells can be subject to human error.

Another well known method is based on flow cytometry which is a method that allows the analysis of a large number of individual cells in a short time. The use of flow cytometric crossmatching of recipient serum against donor lymphocytes has shown it to be a more sensitive method of antibody detection than conventional cytotoxic crosshatch. Further, FACs (fluorescent activated cell sorting) screening of pooled cells can accurately and rapidly detect anti-MA antibodies. It has been shown (Harmer et al., Transpl. Int. (1993) 6: 277-280) that FACS can detect IgG antibodies which have not been detected by conventional screening methods.

However, these prior art methods are constrained due to the presence of molecules other than MA on the whole cells, and therefore other 'non-HLA' antibodies are detected. The recent use of ELISA (enzyme-linked-immunosorbent assay) employing purified class I and class II antigens from platelets and cell lines partially overcomes this problem.

In U.S. Pat. No. 5,948,627 (Lee et al.) the use of a plurality of microbeads presenting multiple purified HLA antigens from a cell population in order to test for anti-HLA antibodies is discussed.

Therefore, there is still a need for an assay for anti-MHC antibodies that detects single specific antibodies in a sample, in a quick and reliable manner. This will enable the dissection of component specificities and the detection of antibodies to rare MHC, e.g. HLA alleles in sera from highly sensitized patients. In brief, an assay is required that will precisely define the anti-MHC antibodies present in a sample, quickly, simply and reproducibly.

SUMMARY OF THE INVENTION

Surprisingly, it has now been found that individual recombinant HLA or HLA-type molecules can be used for specifically detecting anti-HLA antibodies. The recombinant HLA monomers have been found by the inventors to be bound by anti-HLA antibodies in a sample. Thus, recombinant MHC monomers can be utilized in the detection, identification and removal of anti-MHC antibodies. These recombinant MAC or MHC-type monomers, functioning as anti-MHC antibody antigens, have the advantage that the identity of the MHC is known, and that the sample can therefore be tested for anti-MHC antibodies for each individual recombinant MAC or MHC-type. The advantages of a more specific assay method for detecting anti-MHC, e.g. anti-HLA antibodies are self evident and include the advantages of being more convenient, less time consuming and labour intensive to develop and therefore less costly.

Significantly, the use of recombinant MHC or MHC type monomers avoids the need for purifying MHC molecules from a cell population presenting said MHC and is far simpler and quicker than CDC-type methods. The benefits of the method of the invention include the ability to quantify anti-MHC-antibodies present in a sample, in a highly reproducible manner. Uniquely, this assay ensures that the only target present is a specific, individual, MHC antigen. The method of the invention reduces assay time per sample from several weeks, in the came of CDC, to less than 3 hours. Also, as cells are not required for the assay, this circumvents the recently evolved problem of lack of availability of CDC target cells.

DETAILED DESCRIPTION OF THE INVENTION

Thus, in a first aspect the present invention provides a method of detecting the presence of anti-MHC antibodies in a sample comprising contacting said sample with one or more recombinant MHC molecules or functionally equivalent variants, derivatives or fragments thereof and detecting the binding or absence of binding of antibodies to said recombinant MHC molecules, variants, derivatives or fragments thereof. This method allows the detection and/or identification of one or more specific MHC antigen antibodies.

As used herein "detecting" refers to a qualitative, quantitative, or semi-quantitative assessment of the formation of an antibody:MHC molecule complex in the sense of obtaining an absolute value for the amount of complex formed in the sample or an index, ratio, percentage or similar qualitative or semi-quantitative indication. Thus "binding" denotes the formation of a specific and selective interaction between said 2 components. Appropriate means of detection are as described hereinafter and include detection of labels or signalling means associated with said complexes such as the use of antibodies to one of the components, in which the antibodies themselves carry a label or signalling means which can be detected by appropriate techniques. Alternatively the MHC molecules may be designed to inherently carry a label/signalling means e.g. by the use of radiolabelled amino acids in their construction, or added post-synthesis.

The signalling means may in general be any moiety capable of direct or indirect detection, e.g. by virtue of its enzymatic properties, radiation emission, scattering, absorption or magnetic properties or may cooperate with or bind to a complimentary agent to produce a detectable effect, e.g. interact with an enzyme to produce a signal, gas evolution, light emission, colour change, turbidity, precipitation etc. Such moieties are well known within the field of diagnostic assays. Alternatively the signalling means may be or allow association with a label such as radiolabels, chemical labels (for example chromophores or fluorophores such as dyes e.g. fluoroscein and rhodamine) or reagents of high electron density e.g. ferritin, haemocyamin or colloidal gold.

"Identification" refers to the identification of one or more particular MHC allele antibodies based of the specific MHC molecule to which they bind. "Absence of binding" as used herein refers to absence of detectable binding above control levels. Binding is considered to occur and hence signify the presence of a particular MHC allele when levels above a determined threshold relative to control levels are observed.

As used herein "recombinant" refers to a molecule or part thereof (preferably the MHC heavy chain) that has been produced in one or more cells via genetic engineering of that cell. Thus, the cell has been genetically modified relative to its naturally occurring form and has been provided, by any suitable means, with all the genetic information necessary to produce, or produce greater quantities of, the molecule of interest. Preferably the cell is a prokaryotic cell (e.g. bacterial cells, e.g. $E.$ $coli$ derivatives) or a simple eukaryotic cell (e.g. yeast, plant or insect cells). It is possible to produce recombinant molecules in higher organisms, i.e. mammals, but it will be understood by those skilled in the art that such methods are more labourious and time consuming than recombinant molecule production in unicellular organisms.

Preferably cells are modified by introduction of a vector (e.g. a plasmid) which may replicate separately to the genome of the cell or may be integrated into that genome. In the case of expression of class I molecules the vector comprises for example a nucleic acid molecule encoding all or part of the MHC heavy chain operatively linked to elements suitably controlling its replication, transcription and/or translation. Additionally, when preparing a class I MHC molecule the same or a further genetically modified cell may be utilised which expresses $\beta_2$-microglobulin. When preparing a class II MHC molecule the vector comprises the α and/or β chain under suitable regulatory control. In essence, the component of the MHC molecule that dictates the variability and hence polymorphism of MHC alleles is expressed recombinantly, whereas non-variant molecules, e.g. $\beta_2$-microglobulin may be purified, although preferably all components are expressed recombinantly.

The recombinant MHC or MHC-type molecule used in the method of the invention can be either class I or class II, but must be sufficiently antigenic in order to be bound by anti-MHC antibodies. Preferred Class I molecules are A, B and C, although other possible molecules are E, F, G, MICA, MICB and CDI. Preferred Class II molecules are DRB1/3/4/5, DQA1, DQB1, DPA1 and DPB1. The recombinant MHC or MHC-type molecule therefore has to present the extracellular polymorphic residue (i.e. the residue that is altered in each HLA type) for binding by the anti-MHC antibody.

As used herein an MHC molecule for use in the method of the invention, is preferably an HLA molecule and includes functionally equivalent variants, derivatives or fragments thereof. The MHC molecule and its variants, derivatives or fragments may comprise more than one component which together form a complex with antigenic properties, e.g. in the case of Class I molecules, the heavy chain, $\beta_2$-microglobulin and a peptide. Thus the sequence of naturally occurring MHC molecules may be modified providing areas which make up at least one unique epitopic site (which may be provided by one or more of the components of the MHC molecule), particularly regions of variability which allow presentation of at least one unique epitopic region which typifies a particular MHC allele and which results in the production of specific MHC antibodies directed to that region are maintained such that the said specific antibodies are still capable of binding to that region. As will be appreciated this requires maintenance of not only residues at the epitopic site, but also key skeletal residues to achieve correct folding of the MHC molecule to form the epitopic site. However, the use of misfolded MHC molecules in the method of the invention is also envisaged, wherein the epitopic site remains available for antibody binding.

Thus derivatized MHC molecules are also contemplated providing they exhibit the same function, i.e. allow appropriate presentation of one or more of the epitopic sites of the MHC allele of interest. Thus functionally equivalent variants, derivatives or fragments refer to MHC molecules related to or derived from naturally occurring MHC molecules wherein the amino acid sequence of one or more components of said MHC molecules (e.g. the class I heavy chain, class IIα and/or β chain) has been modified by single or multiple amino acid (e.g. at 1 to 50, e.g. 10 to 30, preferably 1 to 5 bases) substitution, addition and/or deletion but which nonetheless retains functional activity.

Within the meaning of "addition" variants are included amino and/or carboxyl terminal fusion proteins or polypeptides, comprising an additional or replacement protein or polypeptide fused to the polypeptide sequence e.g. a portion of the MHC molecule (e.g. the MHC class I heavy chain transmembrane/cytosolic tail) is preferably supplemented or replaced with a means for immobilisation, e.g. a peptide which allows biotinylation of said molecule.

Derivatives may be prepared by post-synthesis modification or by modification during synthesis e.g. using modified residues or modified encoding nucleic acid material e.g. modified by site-directed mutagenesis. Derivatives preferably include those in which conservative amino acid substitutions are employed so as not to significantly affect structure and function at that residue. Derivatized or modified amino acids may also be used, e.g. methylated residues, where compatible with recombinant expression.

Preferably, the derivatives and variants are closely related to one or more components of the naturally occurring MHC molecules, e.g. are encoded by nucleic acid molecules with more than 70%, preferably more than 80, 90 or 95% sequence identity to naturally occurring sequences or exhibit such sequence identity to the functional portions of these sequences, e.g. to naturally occurring allelic geographical or allotypic variants e.g. to sequences as described in the MGT website ("ebi.ac.uk/img/hla"). Preferably said derivatives or variants exhibit the above-stated sequence identity to sequences identified in "Nomenclature for factors of the HLA system, 1998, Tissue Antigens 1999: 53, 407-446". Such derivatives or variants may be for example, as described in the website ("ebi.ac.uk/img/hla") or Table 4. Alternatively stated, the encoded polypeptides may exhibit more than 70%, preferably more than 80, 90 or 95% sequence identity or exhibit such sequence identity to the functional portions of these sequences, e.g. to naturally occurring sequences as described in the IMGT website ("ebi.ac.uk/img/hla"). Preferably said derivatives or variants exhibit the above-stated sequence identity to sequences disclosed in "Nomenclature for factors of the HLA system, 1998, Tissue Antigens 1999: 53, 407-446". Such derivatives or variants may be for example, as described in the website ("ebi.ac.uk/img/hla") or Table 4.

"Sequence identity" as referred to herein in connection with nucleotide sequences refers to the value obtained when assessed using ClustalW (Thompson et al., 1994, Nucl. Acids Res., 22, p4673-4680) with the following parameters:

Pairwise alignment parameters—Method: accurate,

Matrix: IUB, Gap open penalty: 15.00, Gap extension penalty: 6.66;

Multiple alignment parameters—Matrix: IUB, Gap open penalty: 15.00, % identity for delay: 30, Negative matrix: no, Gap extension penalty: 6.66, DNA transitions weighting: 0.5.

In connection with amino acid sequences, "sequence identity" refers to sequences which have the stated value when assessed using ClustalW (Thompson et al., 1994, supra) with the following parameters:

Pairwise alignment parameters—Method: accurate,

Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR (SEQ ID NO:1). Sequence identity at a particular residue is intended to include identical residues which have simply been derivatized.

Functionally equivalent fragments according to the invention may be made by truncation, e.g. by removal of regions of components of the MHC molecule not crucial to formation of one or more epitopes on said recombinant MHC molecule. Thus fragments may, as with MHC molecules comprise more than one component. Such fragments may be derived from naturally occurring molecules as described above or from the functionally equivalent variants or derivatives thereof. Preferably the fragments are between 50 and 500 residues, e.g. 100 and 250 residues in length.

Preferably said MHC molecules are, or are derived from, humans, domestic animals or livestock, such as cats, dogs, horses, donkeys, Cheep, cows, goats, rabbits, rats, mice, monkeys or apes, although preferably the MHC molecules are HLA molecules, i.e. derived from humans. Preferably said MHC molecules (or derivatives, variants or fragments thereof) are class I molecules. The invention does however also extend to class II MHC molecules. Especially preferably the MHC molecules are in monomeric form. Said monomeric form however refers to the minimum number of components necessary to display one or more epitopes corresponding to an epitope of a naturally occurring MHC allele, e.g. a heavy chain, β-microglobulin and an associated peptide. However, for class In MHC molecules, less components may be necessary to form the epitope. Therefore, it may not be necessary to include the associated peptide, for example, for class II molecules.

The method of the invention employs recombinant MHC or MHC-type monomers in order to detect anti-MHC antibodies. A number of recombinant HLA or HLA-type molecules are known and described in the literature. As mentioned above, any of these or their fragments, may be used according to the present invention as indeed may any molecule, or fragment thereof, exhibiting the properties and characteristics of an HLA molecule ("HLA-type") as described further below.

Tetramers of human lymphocyte antigen A2 complexed with two differed HIV-derived peptides or a peptide derived from influenza A matrix protein are described in Altman et al., 1996, Science, 274, 94-96. In this paper, recombinant multimeric peptide-MHC complexes are synthesized in order to bind to T cells. Tetramers of recombinant HLA-2 complexed with any one of the three peptides mentioned above were used. However, in the method of the invention it is envisaged that monomers of recombinant HLA or HLA-type molecules will preferably be used. The tetrameric complexes of recombinant HLA class I are further described in Ogg et al., J. Exp. Med., 1998, 188, 1203 to 1208 the disclosure of which is herein incorporated by reference. In this paper, the HLA heavy chain was expressed in *Escherichia Coli*.

In a preferred embodiment of the invention, the recombinant MHC is synthesised in a prokaryotic expression system (see Example 1). It will therefore be understood by those skilled in the art that the MHC molecule will be synthesised in an un-glycosylated form, as prokaryotic cells do not have the capacity to glycosylate proteins. Glycosylated sites are known to play important roles in ligand binding, and would therefore be thought to be a necessary component of anti-MHC antibody binding to MHC molecules. Surprisingly, the inventors have discovered that the lack of glycosylation of the recombinant HLA or HLA-type molecules is not detrimental to anti-HLA antibody binding.

In the method of the invention, any suitable recombinant MHC or MHC-type monomer may be used. It may be necessary to complex the recombinant MHC with a peptide in order to present the recombinant MHC/MHC-type monomer for anti-MHC antibody binding, and this forms a preferred aspect of the invention especially with respect to class I MHC molecules, fragments or derivatives thereof. Any suitable peptide may be used in the complex, but it will be understood that, in order to prevent antibodies in the sample specific for the complexing protein binding to the complexing protein, it is preferable to use a peptide against which most individuals do not possess antibodies. Thus peptides may be used which are ubiquitous or preferably to which the majority of a given population or a particular individual has not been exposed.

Suitable peptides include peptides of viral origin such as from the HIV (Human Immunodeficiency virus) HCV (hepatitis C virus) or influenza viruses or particular strains of the latter to which most individuals have not been exposed. Preferably the peptide is HIV or HCV derived. It will therefore be necessary to ascertain whether the individual is HIV, HCV or influenza positive prior to analysis of anti-MHC antibodies. Thus, a recombinant MHC or MHC-type monomer completed to HIV, HCV or influenza virus derived peptides form a further aspect of the invention. Preferably said peptide is between 5 and 20 residues, e.g. between 8 and 15 residues, e.g. as described in Example 1.

In order to detect the binding of anti-MHC antibodies to the recombinant MHC molecules, it is preferred to attach the monomers to a solid support, via any suitable linkage. As used herein "linkage" refers to any interaction between the MHC molecule and the solid support, enabling them to be associated. Such interaction may involve physical association such as covalent binding and may also involve so-called "weak" interactions such as hydrogen bonds, Van der Waals forces and ionic interactions. Alternatively, the MHC molecules may be provided with means for attachment to a solid support. Such means may constitute or comprise, for example one partner of an affinity binding pair, e.g. biotin, binding to the corresponding binding partner of the affinity binding pair, i.e. streptavidin, provided on the solid support. Alternative binding pairs include antibodies:antigens and DNA:DNA binding proteins. The HLA molecules may inherently comprise one of said partners, e.g. an epitope or may be synthesized to contain said partner.

It forms a preferred aspect of the invention that the recombinant MHC or MHC-type molecule is synthesized to contain an enzymatic biotinylation site, such as Bir A. The monomer may then be biotinylated using Bir A, biotin, ATP and $Mg^{2+}$. The biotin enables the MHC monomer to bind to streptavidin-coated solid support, for example a solid support such as glass, plastic, tissue culture plastic, a matrix such as sepharose, solid supports such as iron or other metals, a solid particle such as for example a magnetic or non-magnetic bead.

Where appropriate binding partners or the MHC molecules may be attached to the solid support by any convenient means e.g. attachment by methods well known in the art such as attachment through hydroxyl, carboxyl, aldehyde or amine groups which may be provided by treating the solid support to provide suitable surface coatings.

The solid support may be any of the well known supports or matrices which are currently widely used or proposed for immobilisation, separation etc. As mentioned above, these may take the form of particles, sheets, dip-sticks, gels, filters, membranes, fibres, capillaries, or microtitre strips, tubes, plates or wells etc.

Conveniently the support may comprise glass, silica, latex or a polymeric material such as for example nitrocellulose, agarose, alginate, teflon, latex, polystyrene or nylon. Preferred are materials presenting a high surface area for binding. Such supports will generally have an irregular surface and may be for example be porous or particulate eg. particles, fibres, webs, sinters or sieves. Particulate materials e.g. beads are generally preferred due to their greater binding capacity, particularly polymeric beads.

Conveniently, a particulate solid support used according to the invention will comprise spherical beads. In an alternative preferred feature the solid support is nitrocellulose e.g. a strip. In a further alternative preferred feature the solid support is an ELISA plate.

Non-magnetic polymer beads suitable for use in the method of the invention are available from Dynal Particles AS (Lillestrøm, Norway) as well as from Qiagen, Pharmacia and Serotec.

However, to aid manipulation and separation, magnetic beads are preferred. The well-known magnetic particles sold by Dynal Biotech AS (Oslo, Norway) under the trade mark DYNABEADS, are particularly suited to use in the present invention.

The attachment of the recombinant MHC or MHC-type molecule to a solid phase allows easy manipulation of the monomer. Thus, the attachment to some kind of solid phase can enable the separation of the anti-MHC antibodies from the rest of the components in the sample. This can be achieved for example by carrying out washing steps, or if the components are attached to magnetic beads, using a magnetic field to effect physical separation of the linked component from the rest of the components in the mixture.

Therefore, in a preferred embodiment of the method of the invention, the individual recombinant MHC or MHC-type monomer is attached to a solid support, and is contacted with a sample from an individual.

Alternative methods are however contemplated in which detection of antibodies binding to MHC molecules is not achieved using immobilized MHC molecules, Essentially, the assay described herein relies on specific binding between recombinant MHC molecules and antibodies thereto and this complex may be detected by any convenient means e.g. by binding a Further labelled molecule specific for that complex or able to bind to and be used to remove said complex from the sample or techniques which identify complex formation per se, e.g. techniques which discriminate on the basis of size.

The sample for use in the invention may be any suitable sample that contains antibodies, and is preferably a body fluid sample, i.e. blood, blood-derived samples, (e.g. plasma or serum), saliva, interstitial fluid, lymphatic fluid or eluate from cells or tissues. The sample may be used as collected or prepared or diluted where appropriate. The sample is contacted with MHC molecules for a time and under conditions appropriate for the formation of MHC molecule:antibody complexes. The individual from whom the sample is derived corresponds at least by genus, preferably by species, to the MHC molecules to be used in the assay, and are preferably human.

Where a solid support is used, after contact of the sample with the solid support carrying the MHC molecules the solid support is then washed or the physical separation of solid support and sample is effected, in order to remove unbound antibodies and the sample, leaving the relevant anti-MHC antibody bound to individual recombinant MHC monomer attached to the solid support. In a preferred embodiment of the invention, different individual recombinant MHC or MHC-type molecules e.g. relating to one or more epitopes of a naturally occurring allele are bound in individual discrete wells on a microtitre plate, to allow a 'one well-one antigen' format, which allows the testing of a sample for multiple anti-MHC antibodies, delivering an accurate and precise picture of which antibodies are present.

Any means known in the art can be used to detect the antibody bound to the recombinant MHC or MHC-type molecules. When sensitized to foreign MHC molecules, an individual produces antibodies of both immunoglobulin G and M types (IgG and IgM) and other isotypes such as Immunoglobulin A (IgA). The significance of IgM and IgA antibodies directed against MHC in transplantation is not completely understood. However, the presence of anti-MHC IgG antibodies in a patient has been demonstrated to increase the risk of graft rejection. Using appropriate recognition steps it is possible to differentiate between anti-MHC IgG or IgA antibodies and anti-MHC IgM antibodies bound to MHC molecules in accordance with the invention. Both IgG and IgM may be detected in a single assay of the invention, alternatively, the presence of IgG or IgM can be independently determined.

The preferred method of detecting antibody bound to the recombinant MHC monomer, is via ELISA (enzyme-linked immunosorbent assay) and related methods, which involves the use of anti-IgG or anti-IgM antibody conjugated to a so signalling means, e.g. a label or an enzyme (such as horseradish peroxidase). In the latter case, upon addition of a known quantity of substrate for the conjugated enzyme (such as p-nitrophenyl phosphate disodium), the presence and quantity of bound antibody can be ascertained, as well known in the art. As will be appreciated the source of the anti-IgG/IgM antibodies are appropriately selected in line with the IgG/IgM to be detected, e.g. in a human-derived sample anti-human anti-IgG or anti-IgM antibodies are used, e.g. as may be generated by challenge of e.g. rats, mice, or rabbits with human IgG/IgM.

However, any standard method of detecting antibodies may be used in the method of the invention to detect anti-MHC antibodies bound to MHC molecules optionally attached to a solid support, such as the use of colloidal gold conjugated to protein A, immunoelectron microscopy, flow cytometry or immunofluorescent detection.

The method of the invention can primarily be used to detect anti-MHC antibodies, particularly anti-HLA antibodies in the body fluid sample of an individual prior to or after transplantation or blood transfusion. The advantage of the method of the invention over the prior art includes speed, reliability, accuracy and lack of dependency on cells or cell derived products. Thus in further aspects of the invention, the invention provides a method of assessing MHC, preferably HLA compatibility, between 2 individuals comprising the steps of detecting one or more anti-MHC antibodies in a sample from said first individual according to the method described hereinbefore and comparing the results thus obtained to the MHC alleles present in said second individual.

In a further embodiment, the recombinant MHC or MHC type molecules bound to the solid support are utilized when treating blood derived products prior to analysis or processing to produce a blood product—i.e. purified plasma, for transfusion. The blood product may then be suitable for introducing into a recipient. Thus in a further aspect the invention provides a method of depleting a sample of MHC molecule antibodies comprising at least the steps of contacting said sample with one or more recombinant MHC molecules or functionally equivalent variants, derivatives or fragments thereof, optionally attached to a solid support and removing at least the recombinant MHC molecules to which antibodies contained within the sample have bound. The invention further extends to products thus formed. As referred to herein, "depleting" refers to reduction, preferably complete removal of said antibodies.

In the method of the invention, any number of recombinant MHC or MHC type molecules may be used individually to assess the anti-MHC antibodies present in the sample. The use of multiple individual molecules is preferred, obtaining a complete picture on the anti-MHC antibodies. Preferably 1 to 100, more preferably 1 to 75, more preferably 1 to 50 and most preferably 1 to 35 e.g. 10 to 75 or 15 to 30 recombinant MHC or MHC type Class I or II monomers are used in the method of the invention. In a preferred embodiment, at least 30, e.g. 30 to 35, e.g. 33 recombinant MHC or MHC type class I monomers are used. Table 4 shows comprehensive coverage for the method of the invention for anti-Class I HLA antibodies. The invention further extends to a single solid support carrying more than 2, preferably more than 10 different recombinant MHC molecules or functionally equivalent variants, derivatives or fragments thereof at discrete locations on said solid support which may be processed separately according to the method of the invention to allow separate detection and identification of antibodies directed to each of said MHC molecules. Conveniently said support is in the form of a filter or plate with discrete sites or wells and a different MHC molecule is bound to each site or well and the binding of antibodies at each of said sites or wells is determined.

TABLE 4

Comprehensive allele coverage for future monoLISA screening. This list comprises the alleles equivalent to those which would be regarded as providing a broad coverage of HLA class I specificities in a standard CDC test. Alleles in bold are predicted to be the minimum required for monoLISA in the first instance.

| A locus | B locus | C locus |
| --- | --- | --- |
| A*0101 | B*0702 B*4402 | Cw*0102 |
| A*0201 | B*0801 B*4501 | Cw*0202 |
| A*0301 | B*1302 B*4601 | Cw*0304 |
| A*1101 | B*1401 B*4701 | Cw*0303 |
| A*2302 | B*1402 B*4801 | Cw*0401 |
| A*2402 | B*1501 B*4901 | Cw*0501 |

TABLE 4-continued

Comprehensive allele coverage for future monoLISA screening. This list comprises the alleles equivalent to those which would be regarded as providing a broad coverage of HLA class I specificities in a standard CDC test. Alleles in bold are predicted to be the minimum required for monoLISA in the first instance.

| A locus | B locus | | C locus |
|---------|---------|---------|---------|
| A*2501  | B*1502  | B*5001  | Cw*0602 |
| A*2601  | B*1503  | B*5101  | Cw*0701 |
| A*2902  | B*1509  | B*5201  | Cw*0802 |
| A*3001  | B*1512  | B*5301  | Cw*1202 |
| A*3101  | B*1513  | B*5401  | Cw*1203 |
| A*3201  | B*1516  | B*5501  | Cw*1402 |
| A*3301  | B*1801  | B*5601  | Cw*1502 |
| A*3401  | B*2705  | B*5701  | Cw*1601 |
| A*3601  | B*3501  | B*5801  | Cw*1701 |
| A*4301  | B*3701  | B*5901  | Cw*1801 |
| A*6601  | B*3801  | B*6701  |         |
| A*6801  | B*3901  | B*7301  |         |
| A*6901  | B*4001  | B*7801  |         |
| A*7401  | B*4002  | B*8101  |         |
| A*8001  | B*4101  | B*8201  |         |
|         | B*4201  |         |         |

The invention also comprises kits for use in the methods of the invention, which will normally include at least the following components:

a) one or more recombinant MHC molecules or functionally equivalent variants, derivatives or fragments thereof;

b) optionally a solid support, together with means for attachment of the MHC molecules; and c) a means for detecting anti-MHC-antibodies, preferably an antibody which binds to the complex formed between said MHC molecules and naturally occurring antibodies to said molecules, e.g. anti-IgG or anti-IgM antibodies, preferably anti-human anti-IgG or IgM antibodies.

The invention will now be described by way of non-limiting examples with reference to the drawings in which:—

Figure 1:
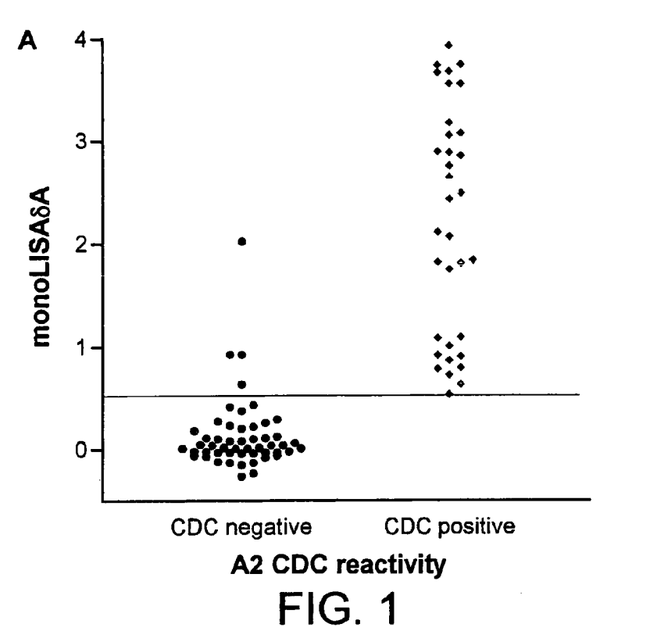
FIG. 1 is a scatter plot of monoLISA δA versus CDC reactivity showing the correlation between CDC and δA for HLA-B8 reactivity.
Figure 2:
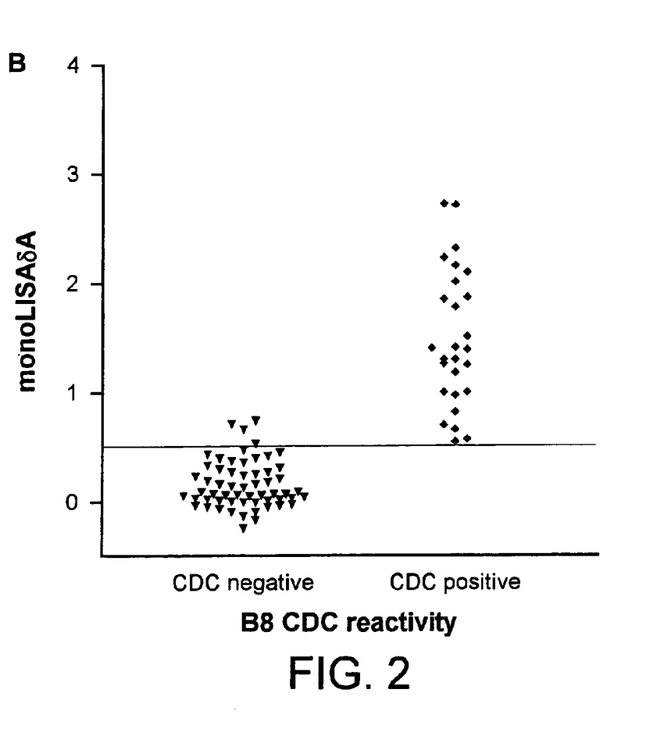
FIG. 2 is a scatter plot of monoLISA δA versus CDC reactivity showing the correlation between CDC and δA for HLA-B8 reactivity.
Figure 3:
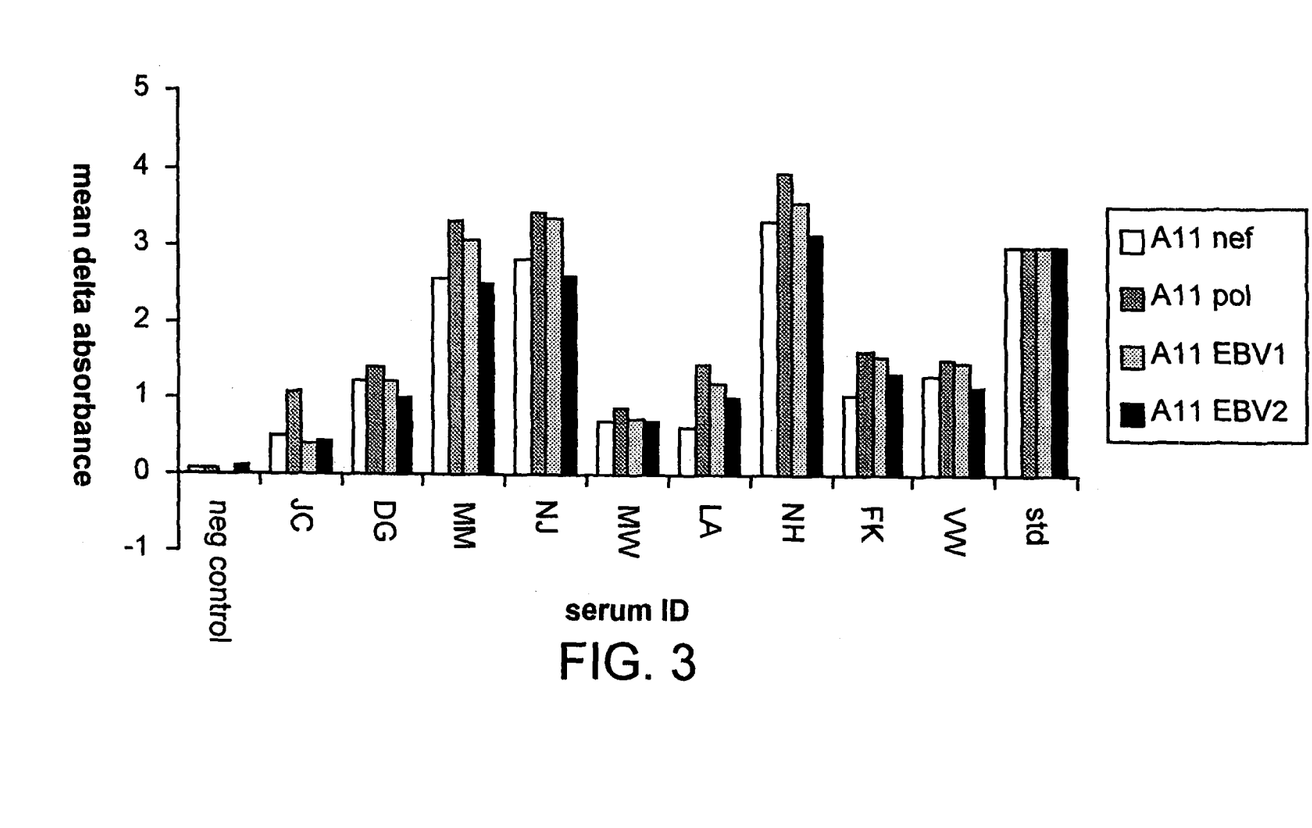
FIG. 3 is a bar graph which shows the influence of presented peptide on Anti-HLA/monomer activity.
Figure 4:
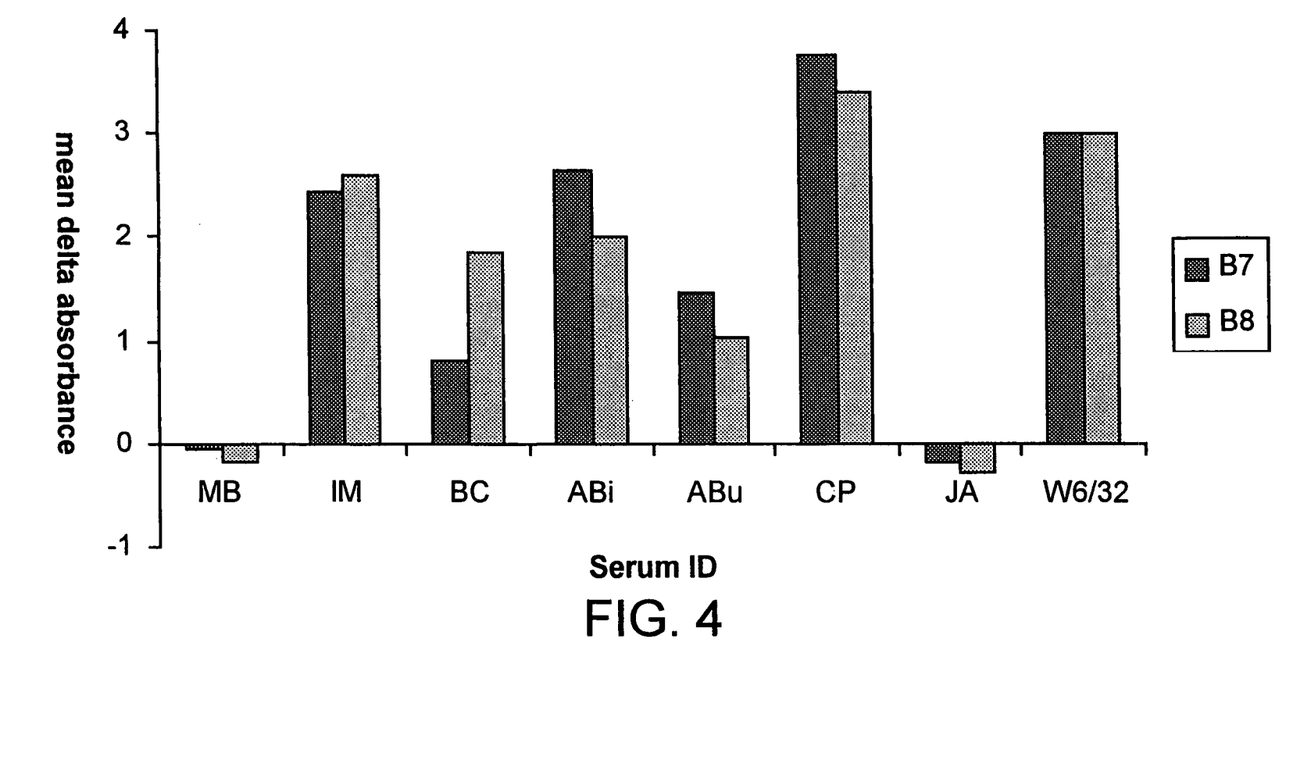
FIG. 4 is a bar graph which shows the influence of glycosylation on anti-HLA antibody binding to the monomer.

FIG. 1 shows the correlation between CDC and monoLISA δA for HLA-A2 reactivity, as a scatter plot of δA versus CDC reactivity. MonoLISA and CDC were performed on 85 sera from renal dialysis or transplant patients and the corrected data (δA) are plotted. An arbitrary cut-off value of 0.5 was applied. The experimental conditions are defined in Example 2;

FIG. 2 shows the correlation between CDC and monoLISA δA for HLA-B8 reactivity, as a scatter plot of δA versus CDC reactivity. The experimental conditions are as defined in FIG. 1;

FIG. 3 shows the influence of presented peptide on anti-HLA/monomer binding. Ten sera were tested in duplicate against a panel of 4 recombinant HLA/peptide complexes made up of A*1101 monomers refolded around either HIV- or EBV-derived peptides. Mean δA values are shown here, on a plot of mean delta absorbance versus serum 1D;

FIG. 4 shows the influence of glycosylation on anti-HLA antibody binding to the monomer, as described in Example 4. Seven sera were tested in duplicate against two monomer/peptide combinations expressing the Bw6 motif (B*0702/EBV and B*0801/HCV). These sera were from 5 patients with CDC-defined anti-Bw6 reactivity, one unsensitized male (MB) and one Bw4-reactive individual (JA). Standardization between the two monomers was carried out by measuring W6/32 reactivity. Mean δA values for the two different monomer/peptide complexes are shown on a plot of mean delta absorbance v serum ID.

Example 1

Materials and Methods
Recombinant HLA Molecules

Purified HLA heavy chain and β2 microglobulin were synthesized using a prokaryotic expression system (pET; Novagen, Milwaukee, Wis.). The heavy chain was modified by deletion of the transmembrane/cytosolic tail and COOH-terminal addition of a 15 amino acid sequence containing the BirA enzymatic biotinylation site. The heavy chain, β2 microglobulin and peptide were refolded by dilution. The 45-kD refolded product was isolated using fast protein liquid chromatography and biotinylated on a single lysine within the BirA substrate peptide, by BirA (Avidity, Denver, Colo.) in the presence of biotin (Sigma Chemical Co., St. Louis, Mo.), ATP (Sigma Chemical Co.) and $Mg^{2+}$ (Sigma Chemical Co.). The biotinylated product was separated from the free biotin by gel filtration and ion exchange using FPLC. The monomers used had been refolded with the peptides listed in table 1. The use of monomers refolded with HIV- and HCV-derived peptides avoided the possible confounding contribution of antibody specific for the peptide rather than the alloantigen. In this manner, HLA-A2, MA-A11, MA-B7 and HLA-B8 monomers (Class I HLA molecules) were synthesized. Two different monomer/peptide combinations were used as target antigens, Az/gag and B8/HCV.

TABLE 1

Details of recombinant monomer/peptide combinations used.

| Monomer ID | Allele | Peptide sequence |
|------------|--------|------------------|
| A2/gag (6) | A*0201 | SLYNTVATL (9) (SEQ ID NO: 2) |
| B7/EBV     | B*0702 | RPPIFIRRL (10) (SEQ ID NO: 3) |
| B8/HCV (8) | B*0801 | HSKKKKDEL (11) (SEQ ID NO: 4) |
| A11/nef    | A*1101 | QVPLRPMTYK (12) (SEQ ID NO: 5) |
| A11/pol    | A*1101 | AIFQSSMTK (13) (SEQ ID NO: 6) |
| A11/EBV1   | A*1101 | IVTDFSVIK (SEQ ID NO: 7) |
| A11/EBV2   | A*1104 | AVFDRKSVIK (14) (SEQ ID NO: 8) |

Solid Support

50 μl of HLA monomer (at approximately 0.5 ng·μl$^{-1}$) was incubated in a streptavidin-coated 96 well 'combiplate' (Labsystems, Finland) at 22° C. for 30 minutes. All volumes were per well, and the monomers were conjugated to the streptavidin-coated microtitre plates in a "one well, one antigen" format. The plate was washed 4 times with 200 μl wash buffer (PBS with 0.05% Tween 20), Example 2

Materials and Methods
Serum Samples

Test sera were separated from the clotted blood of 100 transplanted and pre-transplant renal patients (test sera), and the negative control for both assays was from an untransfused blood group AB male. All patients were tested and were negative for HIV, and sera from patients positive for HCV were excluded from this study. All sera were stored at −20° C. The sera were selected for the presence of IgG of the following specificities as determined by complement-dependent cytotoxicity (CDC): 26 anti-HA-A2 sera, 28 anti-ALA B8 sera and 25 sera showing either no alloreactivity (cytotoxic negativity), or alloreactivity to other Class I molecules (irrelevant antibody). Four of the sera with relevant IgG specificity contained antibodies with specificity for both HLA-A2 and HLA-B8.

ELISA Assays of Serum Samples—"MonoLISA"

The serum was diluted 1:20 in dilution buffer (wash buffer with 5% skimmed milk powder, Tesco Ltd, UK), and then incubated at 22° C. for 30 minutes, on the HLA-coated 'Combiplate', prepared as described in Example 1. The plate was then washed 3 times with 200 µl wash buffer (supra). Each well was incubated for 1 hour at 22° C. with 100 µl of sheep anti-human IgG antiserum conjugated to horseradish peroxidase (Serotec, UK) diluted 1:10000 in dilution buffer and then washed 3 times as above. One hundred microliters of 1 mg-ml$^{-1}$ orthophenylenediamine dihydrochloride (Sigma, UK) solution in phosphate-citrate buffer with sodium perborate (Sigma, UK) was added and incubated for 15 min. at 22° C. in the dark. The reaction was stopped with 100 µl of IN HCl and the absorbance (A) evaluated at 490 nm with a reference wavelength of 630 nm using a Dynatech MRX plate-reader.

Results were corrected (δA) for non-specific binding (background) by subtracting the absorbance of the blank well, which contained serum but no antigen, ($A_{no\ antigen}$) from that of the test well ($A_{test}$). Preliminary data (not shown) led to the assigning of an arbitrary cut-off value for δA of 0.5. To standardize the concentration of different monomers, the above method was carried out identically, except that the mouse monoclonal, W6/32 (Serotec, UK) at a concentration of 1:1000 in dilution buffer, was substituted for patient's serum. Consequently, a rat anti-mouse IgG2a monoclonal conjugated to horseradish peroxidase (Serotec, UK), also at 1:1000 in dilution buffer was used in place of the anti-human conjugate. The monomer was bound at a range of doubling dilutions, and the concentration giving a δA closest to a standard value (3 absorbance units) was chosen as the working concentration for that monomer.

Example 3

CDC-Defined Specificity and δA Values

Table 2 shows the CDC-defined specificity and δA for each of the 85 sera after testing against the A2/gag and BB/HCV monomers. These same data are presented graphically as categorical scatter plots in FIGS. 1 and 2, respectively. Briefly, 4/85 CDC-A2-negative sera were positive with the A2 monomer whilst no CDC-A2-positive sera were negative with A2 monomer. The remaining 81 sera were concordant between the two is methods, with 34 double positive sera and 47 double negatives. With the B8 monomer, there were 4 CDC-B8-ve/monoLISA+ve sera and, again, no CDC+ve/monoLISA-ve serum, with 27 double positive and 54 double negative sera. The monoLISA test using the AS monomer exhibited 100% sensitivity and 92% specificity compared to CDC. Similarly, the B8 monoLISA attained 100% sensitivity and 93% specificity.

TABLE 2

Comparison of CDC-defined specificities with monoLISA δA values. CDC and monoLISA detection results for 85 sera tested against the HLA-2 and HLA-B8 monomers are shown here. Sera that were negative by CDC but positive with the relevant monomer are highlighted. No sera were positive by CDC but negative by monoLISA.

| Specificities | Cytotoxicity | | MonoLISA | |
|---|---|---|---|---|
| | A2[2] | B8[3] | A2[4] | B8[5] |
| A2, 28 | + | − | 3.92 | 0.43 |
| A2, 9 | + | − | 3.74 | 0 |
| A1, 2, 9, 28 | + | − | 3.73 | 0.16 |
| A2, 3 | + | − | 3.67 | 0.09 |
| A2, 3, 9, 28 | + | − | 3.66 | −0.05 |
| A2, 24, 28 | + | − | 3.55 | −0.1 |
| A2, 28 | + | − | 3.55 | 0.33 |
| A2, 26 | + | − | 3.17 | 0.06 |
| A1, 2, 3, 11, (?24) | + | − | 3.07 | 0.74 |
| A1, 2, 28 | + | − | 3.05 | 0.53 |
| A2, B8 | + | + | 2.89 | 2.16 |
| A2, 28, classII | + | − | 2.55 | 0.23 |
| A2, 28, B7 | + | − | 2.85 | 0.18 |
| A2+ | + | − | 2.75 | −0.01 |
| A2, 28, 10, 34 | + | − | 2.64 | 0.24 |
| A2, 9 | + | − | 2.49 | 0.01 |
| a2, a9 | + | − | 2.43 | 0.02 |
| A2, B8 | + | + | 2.11 | 2.72 |
| A2, 9, 28 | + | − | 2.07 | 0.16 |
| Weak A2 | + | − | 1.84 | 0.19 |
| A2 | + | − | 1.82 | 0.37 |
| A2, B8, B57, DR7, 53 | + | + | 1.81 | 0.55 |
| A2, B8, 44 | + | + | 1.75 | 1.3 |
| A2, Bw4, Aw4 | + | − | 1.09 | 0.13 |
| A2 | + | − | 1.08 | 0.71 |
| A2, 28 | + | − | 1 | 0.02 |
| A2, 28 | + | − | 0.91 | 0.06 |
| A2, B7 CREG | + | − | 0.9 | 0.21 |
| A2 | + | − | 0.86 | 0.05 |
| A11, weak A2 | + | − | 0.79 | 0.01 |
| A2, B7 | + | − | 0.72 | 0.4 |
| Weak A2 | + | − | 0.63 | 0.09 |
| A2, IgM B8 | + | − | 0.53 | −0.05 |
| B8, DR3 | − | + | −0.04 | 2.71 |
| A1, B8 | − | + | −0.26 | 2.32 |
| B8 | − | + | 0.92 | 2.23 |
| B8 | − | + | 0.02 | 2.1 |
| Weak B8 | − | + | 0.05 | 2.01 |
| A1, A9, B8 | − | + | 0.92 | 1.87 |
| B8, 18, 35, 53, 5, 21, 61 | − | + | 2.02 | 1.85 |
| B8, 59 | − | + | −0.03 | 1.78 |
| B8, weak 14, 39 | − | + | −0.03 | 1.51 |
| B7, 8, weak Cw7 | − | + | −0.02 | 1.41 |
| | A2 | B8 | A2 | B8 |
| B8, weak 14,16 | − | + | −0.02 | 1.4 |
| B8, DQ2 | − | + | 0.08 | 1.39 |
| Weak B8 | − | + | 0.06 | 1.3 |
| B8, 16 | − | + | 0.22 | 1.26 |
| B8 | − | + | 0.04 | 1.25 |
| B8, 64, 65 | − | + | 0.29 | 1.18 |
| B8 | − | + | 0.2 | 1 |
| A1, B5, 35, 8, Bw6 | − | + | −0.13 | 1 |
| B8 | − | + | 0.12 | 0.97 |
| Weak B8 | − | + | −0.06 | 0.02 |
| B8, weak B65, DQ2 | − | + | 0.11 | 0.7 |
| B8, CW7 | − | + | −0.06 | 0.66 |
| B8, DR52 | − | − | 0.08 | 0.57 |
| A2, IgM | − | − | 0.04 | 0.56 |
| DR 3, 13 | − | − | 0.1 | 0.47 |
| Negative | − | − | 0.23 | 0.45 |
| Negative | − | − | 0.43 | 0.42 |
| Aw4, Bw4 | − | − | −0.07 | 0.4 |
| A9, B5, 35, 53, 15, 17 | − | − | 0.48 | 0.36 |
| A2 IgM, B44, 40, 41 | − | − | 0.41 | 0.31 |
| B51, 52, 53, IgM B8, Bw4 | − | − | −0.03 | 0.3 |
| Multi B (not B8) | − | − | 0.01 | 0.27 |
| A9, weak A10, A11 | − | − | 0.01 | 0.27 |

TABLE 2-continued

Comparison of CDC-defined specificities with monoLISA δA values. CDC and monoLISA detection results for 85 sera tested against the HLA-2 and HLA-B8 monomers are shown here. Sera that were negative by CDC but positive with the relevant monomer are highlighted. No sera were positive by CDC but negative by monoLISA.

| Specificities | Cytotoxicity | | MonoLISA | |
|---|---|---|---|---|
| A1, 3, 9, 11 | − | − | 0.01 | 0.25 |
| B7, 27 | − | − | 0.11 | 0.14 |
| A10 | − | − | 0.18 | 0.07 |
| B57+ | − | − | −0.04 | 0.07 |
| AB serum (Neg control) | − | − | −0.13 | 0.07 |
| A10, 34, 32, 40, 41, 12, 13 | − | − | 0.63 | 0.06 |
| Weak IgM autos | − | − | 0.04 | 0.05 |
| B17+ autos | − | − | 0.1 | 0.04 |
| B7, DQ1 | − | − | 0.26 | 0.03 |
| Week IgM B8 | − | − | 0.02 | 0.03 |
| B12, A1 | − | − | −0.03 | −0.01 |
| A1, Bw4+ | − | − | −0.15 | −0.03 |
| Probable autos | − | − | −0.02 | −0.04 |
| IgM B8, 17, 27 | − | − | −0.08 | −0.04 |
| DR11, 13, 8, (3, 14), DR52 | − | − | 0.37 | −0.07 |
| Probable autos | − | − | −0.23 | −0.1 |
| (DR13) | − | − | 0.01 | −0.14 |
| Negative | − | − | −0.12 | −0.17 |
| IgM B8, 27 | − | − | 0.27 | −0.25 |

[1]CDC-defined specificities
[2, 3]Presence or absence of CDC A2 and B8 reactivity respectively
[4, 5]δA values obtained with A2 and B8 monomers, respectively Discussion This study demonstrates an excellent correlation between the techniques of CDC and monoLISA. With both the A2 and B8 monomers tested there were positive reactions which had previously been negative by CDC. These reactions, which tended to be relatively weak, are to be expected in a system that is designed to detect IgG isotype-binding and not just the presence of cytotoxic antibodies This phenomenon has previously has been reported using the ELISA method, PRA-STAT which detected HLA-specific IgG antibodies relevant to transplant outcome that were not detected by CDC. More importantly in this study, all the sera that showed positivity in the CDC test were also positive using monoLISA, this is a good demonstration that, at least using the sera tested, there was no abrogation of the antibody/antigen interaction using recombinant molecules in place of the natural ligand.

Example 4

The Influence of Resented Peptide on Anti-HLA/Monomer Binding

To investigate whether the presence of different peptides presented in the monomer would exert any effect on the strength of antibody binding, 4 recombinant HLA/peptide complexes comprising identical monomers but different peptide were used. This panel was available for HLA-A*1101 and included 2 HIV-derived peptides (nef and pol) and 2 EBV-derived peptides (EBVI and EBV2; table 1). These monomer/peptide combinations were applied to sera containing antibodies against HLA-A11 as detected by CDC. To minimize the interference of any possible specific humoral response directed at the peptides, the peptides were derived from pathogens which were either absent from the patient population (HLV) or ubiquitous (EBV). Nine sera from sensitized patients were selected for the presence of anti-A11 antibodies. A negative control serum was also used for the absence of HLA-reactive immunoglobulin. These sera were reacted in duplicate with each of the 4 different A11 monomer/peptide combinations. Each of the monomer/peptides was also standardized with W6/32 in the same plates so that correction could be made for slight variations in actual monomer concentrations.

Results

Each of the 10 sera gave grossly similar results with the different monomer/peptide combinations, and all sera had significantly higher δA values than the negative control (p<0.001, paired T). This demonstrates that bound peptide did not significantly interfere with reactivity in the monoLISA test. The results are depicted graphically as FIG. 3.

Discussion

The use of monomers with identical HLA antigens, but different peptides within the groove offered an opportunity to analyse the importance of the peptide in alloantibody responses. Using a limited number of monomers of the same HLA specificity (A11), but with different peptides, we have demonstrated that the peptide does not have a large impact on alloantibody binding. This is an important observation, as it suggests that single monomers with irrelevant peptides within the groove can be used for antibody screening in this assay.

Example 5

The Influence of Glycosylation on Anti-HLA/Monomer Binding

Prokaryotic expressions systems such as *Escherichia coli* are potentially restricted by their inability to glycosylate proteins. As native HLA class I heavy chains have an N-linked carbohydrate moiety at asparagine 86 it is possible that antibodies specific for epitopes in the proximity of this residue may have differential binding characteristics with recombinant monomers compared to native protein. The Bw4 and Bw6 motifs, present on all expressed HLA-B locus antigens constitute a well-defined operationally dimorphic system. The residues responsible for these motifs are at positions 77-83 on the class I heavy chain. This region of the heavy chain sequence constitutes the most proximal known epitope to the glycosylation site. Anti-Bw6 reactivity was thus used to determine whether the absence of carbohydrate had a measurable effect on the binding of alloantibodies. Antisera of the Bw6 specificity were tested with monoLISA using the two monomers—B7/EBV and B8/HCV as Bw6 motif-bearing targets. Bw4 motif-bearing monomers were not available for testing. Antisera from 5 patients with CDC-defined anti-Bw6 reactivity, one AB serum and one Bw4-reactive serum were tested in duplicate against the two monomer/peptide combinations. Standardization between the two monomers was carried out by measuring W6/32 reactivity as above. The sensitization details of the selected sera are given in table 3.

TABLE 3

| | | Sensitization | |
|---|---|---|---|
| ID | Specificity | Route of known HLA | Transfusions |
| MB | Negative control | None | None |
| IM | Bw6 | B7 tx[1] | None |
| BC | Bw6+ | B7 & 8 tx B7 preg[2] | 14 |
| ABI | Bw6 | None | 7 |
| ABu | Bw6 | None | 4 |
| CP | Bw6 | B7 preg | 7 |
| JA | Bw6 | None | 2 |

[1]tx, kidney transplant;
[2]pregnancy-sensitization determined on the basis of the HLA of the presumed father.

All the sera reacted above the arbitrary cut-off δA of 0.5, and the negative controls both reacted at a lower level than the no-monomer wells. Variation in binding levels between the different sera was apparent, and with the exception of serum BC, the results obtained with the two monomers followed the same trend. These results show that the lack of a carbohydrate moiety did not reduce the binding of antisera to a very close epitope, i.e. the Bw6 motif. Indeed, the absorbance values obtained were mostly high in the range of values seen using sera against other epitopes.

Discussion

The reactivity exhibited by the two Bw6 bearing monomers suggests that the Bw6 motif can be detected using the monoLiSA method. As the putative Bw6 motif is situated close to the carbohydrate-bearing amino acid on HLA class I, this suggests that lack of glycosylation of the monomers is not detrimental to binding, and thus detection, of antibody. The possibility, however, that the selected sera contained not only anti-Bw6 reactivity, but also Antibodies reacting with B7- and B8-specific motifs that are spatially separate from the putative Bw6 region cannot be ruled out. However, this is unlikely, given that similar strengths of reactivity are demonstrated against both molecules with each individual serum. The exception is serum BC. With this serum, the monomers reacted differentially, the B8 eliciting approximately double the reactivity produced with B7. This disparity in reactivity can be explained, as the patient was sensitized with a graft bearing both B7 and B8. A later serum from the same patient showed a decrease in PRA that allowed the two specificities, B7 and B8, to emerge from the broader Bw6 specificity (data not shown). Presumably, the graft-presented BS elicited a stronger response than did B7, to which the patient was exposed on the graft and in previous pregnancies.

The invention claimed is:

1. A method for detecting anti-Major Histo-Compatibility Complex (MHC) antibodies in a body fluid sample, the method comprising:
   contacting the body fluid sample with a solid support comprising discrete sites, each site comprising a different specific, individual recombinant MHC Class I monomers corresponding to one specific, individual MHC Class I antigen; and
   detecting the binding of antibodies to the specific, individual recombinant MHC monomers, wherein binding indicates the presence in the body fluid sample of antibodies to the specific, individual MHC antigen.

2. The method of claim 1 wherein each discrete site is processed separately from the other discrete sites.

3. A kit for detecting in a body fluid sample the presence of one or more anti-Major Histocompatibility Complex (MHC) antibodies against specific, individual MHC antigens, the kit comprising at least the following components:
   a) a solid support comprising discrete sites, each site comprising a different specific, individual recombinant MHC Class I monomers, each monomer corresponding to one specific, individual MHC Class I antigen; and
   b) a moiety capable of direct or indirect detection of anti-MHC-antibodies that bind the recombinant MHC monomers corresponding to the specific, individual MHC antigen of (a),
   wherein binding indicates the presence in the body fluid sample of antibodies to the specific, individual MHC antigen.

4. The kit of claim 3, wherein recombinant MHC monomers corresponding to at least two to 100 specific, individual HLA Class I antigens are bound to discrete sites on the solid support.

5. The method of claim 1, wherein at least two or more sites comprise a MHC Class I heavy chain, β-microglobulin, and a peptide.

6. The method of claim 5, wherein the recombinant MHC Class I heavy chain are synthesized in a prokaryotic expression system.

7. The method of claim 5, wherein the recombinant MHC Class I heavy chain is synthesized in un-glycosylated form.

8. The method of claim 1, wherein at least two or more sites comprise human leukocyte Class I antigens (HLA).

9. The method of claim 8, wherein at least two or more sites comprise a HLA Class I heavy chain, β-microglobulin, and a peptide.

10. The method of claim 9, wherein the HLA Class I heavy chain is synthesized in a prokaryotic expression system.

11. The method of claim 9, wherein the HLA Class I heavy chain is synthesized in un-glycosylated form.

12. The method of claim 5 or 9, wherein said peptide is derived from a human immunodeficiency virus (HIV), a hepatitis C virus (HCV), or an influenza virus.

13. The method of claim 5 or 9, wherein the heavy chain is biotinylated.

14. The method of claim 8, wherein the HLA antigens are selected from the group consisting of A*0101, A*0201, A*0301, A*1101, A*2301, A*2401, A*2501, A*2601, A*2902, A*3001, A*3101, A*3201, A*3301, A*3401, A*3601, A*4301, A*6601, A*6801, A*6901, A*7401, A*8001, B*0702, B*0801, B*1302, B*1401, B*1402, B*1501, B*1502, B*1503, B*1509, B*1512, B*1513, B*1516, B*1801, B*2705, B*3501, B*3701, B*3801, B*3901, B*4001, B*4002, B*4101, B*4201, B*4402, B*4501, B*4601, B*4701, B*4801, B*4901, B*5001, B*5101, B*5201, B*5301, B*5401, B*5501, B*5601, B*5701, B*5801, B*5901, B*6701, B*7301, B*7801, B*8101, B*8201, Cw*0102, Cw*0202, Cw*0304, Cw*0303, Cw*0401, Cw*0501, Cw*0602, Cw*0701, Cw*0802, Cw*1202, Cw*1203, Cw*1402, Cw*1502, Cw*1601, Cw*1701, and Cw*1801.

15. The method of claim 1, wherein the body fluid sample is blood or a blood-derived sample.

16. The method of claim 15, wherein the body fluid sample is purified plasma.

17. The method of claim 1, wherein the solid support is selected from the group consisting of glass, a glass slide, silica, latex, agarose, alginate, teflon, polystyrene, nylon, plastic, tissue culture plastic, a spherical bead, sepharose, a magnetic bead, a non-magnetic bead, a filter, a membrane, a fibre, a capillary, a nitrocellulose strip, a tube, a plate, a plate comprising multiple wells, and an ELISA plate.

18. The method of claim 1, wherein the antibodies are detected using a method selected from the group consisting of an immunosorbent assay using an antibody conjugated to a label or enzyme, detection of colloidal gold, immunoelectron microscopy, flow cytometry, immunofluorescent detection, and ELISA.

19. The method of claim 1, wherein the antibodies are selected from the group consisting of IgG, IgM, and IgA.

20. The method of claim 1, wherein at least two to 100 specific, individual recombinant MHC Class I monomers corresponding to at least one to 100 specific, individual MHC antigens are bound to discrete sites on the solid support.

21. The method of claim 8, wherein at least two to 100 specific, individual recombinant HLA Class I monomers corresponding to at least one to 100 specific, individual HLA Class I antigens are bound to discrete sites on the solid support.

22. The kit of claim 3, wherein recombinant MHC monomers corresponding to at least two to 100 specific, individual MHC Class I antigens are bound to discrete sites on the solid support.

23. The kit of claim 3, wherein the solid support is selected from the group consisting of glass, a glass slide, silica, latex, agarose, alginate, teflon, polystyrene, nylon, plastic, tissue culture plastic, a spherical bead, sepharose, a magnetic bead, a non-magnetic bead, a filter, a membrane, a fibre, a capillary, a nitrocellulose strip, a tube, a plate, a plate comprising multiple wells, and an ELISA plate.

24. The kit of claim 3, wherein the antibodies are detected and identified using a method selected from the group consisting of an immunosorbent assay using an antibody conjugated to a label or enzyme, detection of colloidal gold, immunoelectron microscopy, flow cytometry, immunofluorescent detection, and ELISA.

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: oligopeptide

<400> SEQUENCE: 1

Gly Pro Ser Asn Asp Gln Glu Lys Arg
1               5

<210> SEQ ID NO 2
<211> LENGTH: 9
<212> TYPE: PRT
<213> ORGANISM: Artificial Sequence
<220> FEATURE:
<223> OTHER INFORMATION: oligopeptide

<400> SEQUENCE: 2

Ser Leu Tyr Asn Thr Val Ala Thr Leu
1               5

<210> SEQ ID NO 3
<211> LENGTH: 9
<212> TYPE: PRT
<213> ORGANISM: Artificial Sequence
<220> FEATURE:
<223> OTHER INFORMATION: oligopeptide

<400> SEQUENCE: 3

Arg Pro Pro Ile Phe Ile Arg Arg Leu
1               5

<210> SEQ ID NO 4
<211> LENGTH: 9
<212> TYPE: PRT
<213> ORGANISM: Artificial Sequence
<220> FEATURE:
<223> OTHER INFORMATION: oligopeptide

<400> SEQUENCE: 4

His Ser Lys Lys Lys Lys Asp Glu Leu
1               5

<210> SEQ ID NO 5
<211> LENGTH: 10
<212> TYPE: PRT
```

```
<213> ORGANISM: Artificial Sequence
<220> FEATURE:
<223> OTHER INFORMATION: oligopeptide

<400> SEQUENCE: 5

Gln Val Pro Leu Arg Pro Met Thr Tyr Lys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: oligopeptide

<400> SEQUENCE: 6

Ala Ile Phe Gln Ser Ser Met Thr Lys
1               5

<210> SEQ ID NO 7
<211> LENGTH: 9
<212> TYPE: PRT
<213> ORGANISM: Artificial Sequence
<220> FEATURE:
<223> OTHER INFORMATION: oligopeptide

<400> SEQUENCE: 7

Ile Val Thr Asp Phe Ser Val Ile Lys
1               5

<210> SEQ ID NO 8
<211> LENGTH: 10
<212> TYPE: PRT
<213> ORGANISM: Artificial Sequence
<220> FEATURE:
<223> OTHER INFORMATION: oligopeptide

<400> SEQUENCE: 8

Ala Val Phe Asp Arg Lys Ser Val Ile Lys
1               5                   10
```